United States Patent [19]

Rypácek et al.

[11] Patent Number: 4,808,399
[45] Date of Patent: Feb. 28, 1989

[54] COMPOSITION FOR DIAGNOSING THE TRANSPORT FUNCTION OF THE FALLOPIAN TUBE AND A METHOD FOR PREPARING SAID COMPOSITION

[75] Inventors: Frantisek Rypácek; Jan Uher; Jaroslav Drobník, all of Praha, Czechoslovakia

[73] Assignee: Ceskoslovenska akademie ved, Czechoslovakia

[21] Appl. No.: 940,300

[22] Filed: Dec. 11, 1986

[30] Foreign Application Priority Data

Dec. 11, 1985 [CS] Czechoslovakia ..................... 9078-85

[51] Int. Cl.$^4$ ......................... A61K 9/22; A61K 9/24; A61K 9/26; A61K 9/52; G01N 1/00; G01N 3/48
[52] U.S. Cl. ........................................ 424/2; 514/953; 514/964
[58] Field of Search ....................... 424/2, 19, 20, 22, ; 514/964, 953

[56] References Cited

PUBLICATIONS

Juni, K, Masahiro Nalcano and Miho Kubota, Controlled Release of Aclarabicin, An Anticancer Antibiotic, From Poly-β-hydroxybutyric Acid microspheres, J. Controlled Release, 4(25-32) 1986.

Lee de, L. G. J., le Boer, A. G. and E. Pörtzger Riste-Controlled Rectal Drug Delivery In man with A Hydrogel Preparation, J. Controlled Release, 4(17-24) 1986.

Kwong, A. K., S. Chou, A. M. Sun, M. V. Sefton and M. F. A. Goosen, In Vitro and In Vivo release of Insulin from Poly(Lactic Acid) Micro Beads and Pellets, J. Controlled Release 4(47-62) 1986.

Primary Examiner—Stanley J. Friedman
Attorney, Agent, or Firm—Leydig, Voit & Mayer

[57] ABSTRACT

The present invention pertains to a preparation for diagnosing the transport function of the fallopian tube and to a method for making such a preparation.

The diagnostic preparation for investigation of the transport function of female fallopian tube, comprises a suspension of a biocompatible, biodegradable, and, if desired, labelled particles, in a vehicle commonly used for parenteral applications wherein the particles have a spherical shape with diameters in the region 10 to 600 um, which are formed from a soft hydrophilic gel based on a polymer selected from the group comprising additionally crosslinked water-soluble nontoxic and biodegradable inert polysaccharides and physiologically inert water-soluble and biodegradable poly(amino acids), polypeptides, and their derivatives, which may contain physiologically active substances. The particles retain their shape and size in the environment of peritoneal cavity and uterotubal tract for at least 80 hours with the subsequent degradation to nontoxic product within 5 to 60 days.

A method for preparation of the diagnostic preparation comprises dispersing an aqueous solution of physilogically inert, biodegradable polymer selected from the group of polysaccharides, poly(amino acids), polypeptides, and their derivatives, in a medium of nonpolar water-immiscible solvent, to 10 wt. % of the polymer having a degree of polymerization of 50 to 500, said suspension containing of 80 to 100 mol. % of γ-alkyl-L-glutamate units and 0 to 20 mol. % units of L-glutamic acid, units as a suspension stabilizer, with mixing sufficient to form polymeric spherical particles with diameter 100 to 600 um, which are transferred into the gel state with bifunctional crosslinking agents. The particles are washed and then dispersed in an aqueous solution. The resulting suspension is then sterilized by heat.

9 Claims, No Drawings

COMPOSITION FOR DIAGNOSING THE TRANSPORT FUNCTION OF THE FALLOPIAN TUBE AND A METHOD FOR PREPARING SAID COMPOSITION

BACKGROUND OF THE INVENTION

The invention pertains to a composition for use in diagnosing the transport function of the fallopian tube and to a method for preparing said composition.

The inability of a fallopian tube to transport an ovum, i.e. a blastocyst from the ovarian region into the lumen of uterus, is the frequent reason for female infertility and is estimated to be the cause for one third of all infertile marriages. The reason may be anatomic, e.g., a totally impervious fallopian tube or functional, as when the tube is permeable but the transport does not occur. The latter condition is referred to as functional tubal sterility (FTS) and is usually classified among the so called idiopathic sterilities, the frequency of which is estimated to be 15% of all female infertility. The reason for the disfunction may be various: an inborn hypoplasia, a disorder of muscular activity or a disorder of ovum pick-up. The most frequent reason, however, is the persistent spasm of the isthmic sphincter, which narrows the lumen of this section to 150 um, substantially smaller than the size of the blastocyst which has a diameter of 380 to 400 um.

While a surgical treatment is indicated for anatomic defects, the transport disorders are reparable by conservative procedures. A reliable diagnostic method capable of differentiating between the anatomical and functional source of the problem is therefore needed.

The recent diagnostic procedures employ the ascendent or descendent methods. In the ascendent methods, the fallopian tube is filled by application of a liquid or gas ($CO_2$) into the uterotubal tract. By use of laparoscopy, the penetration of a suitably colored liquid is observed and/or a resistance against the introduced medium is recorded. There has also been described a method utilizing the active transport of radioactive microspheres from human albumin (diam. 10–35 um; labelled with $^{99}$Tc; S.C. Stone et al., Fertil. Steril. 43, 757 (1985)), which were introduced into the vaginal fornix and to the inlet of cervical channel. Hysterosalpingographs were recorded during 60 minutes by means of scintigraphy. The disadvantages of such a procedure consists in the possibility that penetration of the applied medium through a region of spasm (which prevents the transport of the blasocyst) will occur and a false-positive result will be obtained. A detection of a change in pressure (resistance) usually will indicate a spasm during the application under pressure (cineinsufflation), but the spasm may actually have been induced as a consequence of irritation as a result of the procedure, in which case and the result may be a false-negative.

In the descendent methods, a diagnostic medium of particular character is applied into the region of ovaries or into Douglas' space and its penetration into the lumen of the uterus is followed. Chinese ink (D. v. Ott 1925; Ztbl. Gynekol. Nr. 10,546), starch grains (A. Decker and M. Decker, 1954; Obstct. Gynecol. 4, 35), or colloidal radioactive gold ($^{198}$Au) (A. Stabile and F. E. Leborgne, 1958; Int. J. Fertil. 3, 139) are used for this purpose. In the experiments with animals (rabbit), also models of ovum were used in the form of spherical particles of crosslinked dextran (Sephadex) (H. B. Croxatto, C. Vogel, J. Vasquez; J. Reprod. Fert. 33, 337 (1973)) or polystyrene (M. J. K. Harper et al., 1960; J. Reprod. Fert. 1, 249), which can be labelled with radioactive iodine 125I (C. J. Pauerstein and B. J. Hodgson, 1976; Am. J. Obstet. Gynecol. 124, 840).

The aforementioned methods are disadvantageous in clinical application because the particles (Chinese ink, colloidal gold, starch grains) are too small so that they pass through the isthmic region even in the case of persistent spasm. The models of ovum used in the experiments with animals differ in physical properties and surface characteristics from the naturally transported objects on the one hand, and are objected to from the standpoint of patient safety (esp. polystyrene), on the other.

SUMMARY OF THE INVENTION

We have now found that biocompatible spherical particles may be prepared which correspond to the properties of human blastocyst in their size, shape, and mechanical properties, and also partly correspond with respect to biochemical properties, such that they keep their initial properties in the environment of uterotubal tract preferably for at least about 80 hours, and then undergo biodegradation to soluble nontoxic products. We have also found, that if the particles are used in a suitable way, they are actively transported through the fallopian tube which is not harmed thereby. Such particles can be utilized to diagnose the transport function of a human fallopian tube.

The invention provides a diagnostic composition for use in the investigation of the transport function of the fallopian tube. The composition comprises a suspension of biocompatible, biodegradable, and, if it is desired, labelled particles in physiologic saline, or other vehicle commonly used for parenteral applications in medicine, e.g., isotonic solution of sodium chloride or infusion solution of dextran. The particles have a spherical shape with diameters in the region of about 10 to about 600 um, which are formed from a soft hydrophilic gel based on a polymer selected from the group comprising crosslinked water-soluble and biodegradable inert polysaccharides and physiologically inert, water-soluble and biodegradable poly(amino acids), polypeptides, and their derivatives. The particles may contain physiologically active substances, e.g., poly(aminoacids) and/or hormones. The particles are further characterized in that they retain their shape and size in the environment of peritoneal cavity and uterotubal tract for at least 80 hours and then subsequently degrade to nontoxic products within a period of about 5 to about 60 days.

The present invention also provides a method for the preparation of a diagnostic composition, which method comprises dispersing an aqueous solution of a physiologically inert biodegradable polymer selected from the group comprising polysaccharides, poly(amino acids), polypeptides, and their derivatives, which solution may contain an aminoacyl derivative, of a fluorochrome, or a dispersed pigment, or magnetic particles in an amount of about 0.1 to about 10 wt. %, into a medium of nonpolar water-immiscible solvent containing a polymer in an amount fo about 0.1 to about 10 wt. % having a degree of polymerization of about 50 to about 500, consisting of about 80 to about 100 mol. % of γ-alkyl-L-glutamate units and about 0 to about 20 mol. % of L-glutamic acid units, as a suspension stabilizer, to form polymeric spherical particles with diameters in the chosen region of about 10 to about 600 um, and coverting them into a gel state by reaction with a bifunctional crosslinking agent.

DETAILED DESCRIPTION OF THE PREFERRED EMBODIMENTS

The hydrophilic gel particles useful in the present invention are made from a covalently crosslinked water-soluble biodegradable polymer, which is chosen from the group comprising physiologically inert and biodegradable polysaccharides, poly(amino acids), polypeptides, and their derivatives. The suitable polysaccharides contain glucose bound predominantly through 1–4 glycoside bonds, for example, starch, glycogen, amylose, und their biocompatible derivatives, e.g. hydroxyethyl starch. The suitable poly(amino acids) are namely the poly(N-hydroxyethyl)-L-asparagine, poly(N-hydroxyethyl)-L-glutamine, and the copolymers derived from them and containing other amino acids, e.g. the copolymers with L-lysine, L-alanine, and L-valine. The suitable polypeptides are soluble derivatives of collagen and elastin, e.g., gelatine.

The crosslinking agents according to the invention were selected from the group of agents comprising halogenoepoxides, e.g., 2,3-epoxy-1-chloropropane or 2,3-epoxy-1-brompropane, or from the group comprising diisocyanates, e.g., 1,6-hexanediisocyanate and dialdehydes, e.g., glutaraldehyde.

The spherical particles according to the invention may contain substances which enable their identification in biological material. Such compounds according to the invention are usually chromophoric or fluorophoric compounds covalently bound to the polymeric material of the particles, e.g., acylated derivatives of fluoresceine, rhodamine, acridine, and the like, or the microparticles of an inert pigment, e.g., Chinese ink, or magnetic materials, e.g., oxides of iron. The spherical particles of the diagnostic preparation according to the invention may contain substances which influence their biological properties. These substances may be bound to the polymeric material of the particles through a covalent or non-covalent bond and are, for example, poly(amino acids) or polypeptides, as choriogonadotropic hormones and/or substances isolated from follicular liquor.

The nonpolar solvent suitable as a continuous phase of the dispersion is selected from the group of solvents comprising halogenated hydrocarbons, e.g., dichloromethane, dichloroethane, chloroform, cyclic hydrocarbons, e.g., benzene, toluene, and their mixtures. The obtained spherical particles are washed with an alkaline aqueous solution, e.g., with the solution containing 1 to 10 wt. % of sodium hydroxide, in order to saponify γ-alkyl esters of glutamic acid and to decompose any possibly present, unreacted reactive groups of the bifunctional crosslinking agents and the products of their reaction, and the washed particles are dispersed in a suitable solution selected from the group of solutions for parenteral application comprising isotonic solution of sodium chloride, Ringer's isotonic solution, infusion solution of dextran, and the like, which are then sterilized by heat. The resulting spherical particles are chemically activated for binding of biologically active peptides, for example, hormones, by methods commonly used in the immobilization of peptides and proteins on polymeric carriers.

The spherical particles prepared according to the invention are further characterized by the fact, that bonds of the polymer forming the gel are cleaved by the action of enzymes present in uterotubal tract and thus the gel microspheres are gradually dissolved. In this way, the 1,4-glycoside bonds of the polysaccharide forming the gel are cleaved, e.g., by the action of enzymes 1,4-glycosidases, especially α-amylase, the presence of which in a tubal liquor is generally known, with the formation of soluble products containing glucose, glucose oligomers, and their derivatives, which may be either metabolized or excreted. The rate of particle degradation by α-amylase may be controlled, in the procedure according to the invention, by the degree of conversion of the crosslinking reaction, i.e. by the degree of chemical modification and the degree of crosslinking.

The degree of crosslinking depends on the concentration ratio of the bifunctional crosslinking agent and the polymer, the temperature, and the time of reaction. The increased concentration of bifunctional agent and/or the extension of polymerization time leads to the increased degree of crosslinking and to the higher resistance of particles towards biodegradation. In this way, the period of time, for which the particle keeps its shape and size and the time of its persistence in the organism may be controlled in a sufficiently broad region. Similarly, the degree of conversion of the crosslinking reaction of poly(amino acids) and polypeptides, e.g., the concentration ratio of a bifunctional agent, as 1,6-hexanediisocyanate, and gelatine, controls the rate of degradation of the formed gel with proteolytic enzymes, for example, cathepsins, elastase, plasmin, pepsin, etc., which ability to catalyze hydrolysis of the above mentioned poly(amino acids) and polypeptides is generally known.

An advantage of the preparation according to the invention is the ability to perform a diagnostic descendent procedure with particles which approach, by their shape, mechanical, and partly biochemical properties, the properties of human ovum as much as possible. Another advantage is that the particles detained in the body are degraded in a relatively short time to harmless products, whereas the rate of degradation may be influenced within broad limits by the degree of crosslinking of the polymer. It is also advantageous, that the particles can be easily found and identified in a uteral irrigation, so that the probability of false negative or false positive findings is low and the method does not require special apparatus. An additional advantage of the preparation is its easy sterilization as well as the fact that it may carry biologically active components affecting the transport of ovum through the fallopian tube.

EXAMPLE 1

A solution obtained by mixing 7.0 g of soluble starch (mol. wt. 25,000–35,000), 12 ml of distilled water, and 1.2 g of sodium hydroxide (NaOH) was filtered and deaerated in vacuum and 15 ml of this solution was dispersed in 35 ml of 1,2-dichloroethane containing 0.070 g of poly(γ-benzyl-L-glutamate) in a reaction cylindrical vessel equipped with a stirrer and heating jacket. A temperature of 40° C. was kept and the stirrer speed was set in such a way that the average size of obtained particles was 120 to 150 um. Then, 4.0 g of 1-chloro-2,3-epoxypropane (epichlorohydrine) was added and the emulsion was allowed to react under constant stirring at 40° C. for 11 hours. The suspension of particles was then washed by decantation in 300 ml of a cold dichloroethane - dioxane (1:1) mixture and twice in 300 ml of dioxane, and distributed into 4 fractions: (a)

smaller than 40 um, (b) 40 to 120 um, (c) 120 to 240 um, (d) larger than 240 um by sieving in dioxane through screens with mesh size 40 um, 120 um and 240 um. The particles of individual fractions were sedimented, the sediment was dispersed by shaking in 2% sodium hydroxide (NaOH), with occasional shaking for 16 hours at ambient temperature, and then washed with water and physiological saline (0.154 M NaCl). The average size of particles dispersed in the isotonic solution of sodium chloride (NaCl) was determined by optical microscopy. The values 38±12 um, 84±16 um, 205±34 um, and 340±62 um were obtained for the fractions a, b, c, and d, respectively. The content of particles in individual fractions after drying, expressed in percent of the total amount was (a) 3%, (b) 20%, (c) 65%, (d) 12%.

EXAMPLE 2

In a three-neck reaction flask provided with a stirrer, there it was dissolved 3.47 g of 6aminofluoresciene in 120 ml of acetonitrile. The mixture was cooled in a bath to -10° C. and 3.78 g of 3-chloropropionyl chloride along with 4.04 g of triethylamine were gradually added during 30 minutes. The reaction was carried out for 2 hours altogether at $-10°$ C. and the mixture was then allowed to stand at ambient temperature overnight. Acetonitrile was evaporated from the mixture and the residue was dissolved in 300 ml of methanol which contained 17 g of ammonia. The solution of ammonia was allowed to stand at ambient temperature for 3 days. The excess of ammonia was then removed by distillation with methanol, 200 ml of water was added to residue; the ammonium chloride ($NH_4Cl$) which was present was decomposed by addition of sodium hydroxide (NaOH) and the resulting ammonia was distilled off again. The product was obtained after neutralization to pH 6 as a precipitate, which was repeatedly crystallized from water. Yield: 2.75 g of 6-(3-aminopropionamido) fluorescein. For $C_{23}H_{18}O_6N_2.2H_2O$ calculated, C 60.79, H 4.84, N 6.16%; found, C 60.34, H 4.62, N 6.09%.

20 mg of 6-(3-aminopropionamido) fluoresceine and 7.0 g of soluble starch were dissolved in 12 ml of water containing 1.2 g of sodium hydroxide (NaOH); 15 ml of this solution was filtered, degased, and dispersed in 35 ml of 1,2-dichloro-ethane containing 70 mg of poly($\gamma$-benzyl glutamate). The reaction with 4.0 g of 1-chloro-2, 3-epoxypropane (epichlorohydrine) was carried out at 40° C. for 11 hours in the same way as in Example 1 and the prepared particles were fractionated by sieving in dioxane analogously to Example 1. The fraction passing through the screen with mesh size 240 um and retained by the screen with mesh size 120 um was dispersed in 2% solution of sodium hydroxide (NaOH) for 16 hours, when all remaining reactive groups were decomposed, washed with water and an isotonic solution of sodium chloride (NaCl), and then extracted with an isotonic solution of NaCl at pH 7 and 120° C. for 40 min in an autoclave. The particles were then washed with sterile isotonic solution and under aseptic conditions filled into steile serum ampouls and again sterilized in the autoclave at 120° C. for 40 min. They were stored as a sterile suspension in the isotonic solution.

The particles had a regular spherical shape with the size 140 to 280 um and an average value of 195±36 um. At the excitation with blue light ($\lambda=430$ nm), they exhibit a brilliant fluorescence in the yellow-green region 515 to 530nm. The fluorescent label is stable and is not washed out, until the gel degradation occurs.

EXAMPLE 3

Fluroescently labelled microspheres differing in the duration of reaction with 1-chloro-2,3-epoxypropane were prepared at the same ratio of reacting components and under the same reaction conditions as in Example 2, with the distinction that the reaction was stopped in individual samples by dilution of the suspension with a cold mixture of dioxane and 1,2-dichloroethane (1:1) after 7, 9, 11, 13, and 18 hours of reaction at 40° C., respectively. The samples of particles were dispersed in the amount corresponding to 10 mg of dry substance in 2 ml of physiologic saline with pH 7.4, which contained 115 U/ml of pancreatic $\alpha$-amylase, and incubated at 37° C. under moderate shaking. Time required for the complete dissolution of particles was followed in a fluorescent microscope. The stability of particles in the medium containing $\alpha$-amylase increases with the extended reaction time with epichlorohydrine; see Tab. 1.

TABLE 1

| Sample | Reaction Time (h) | Time Required for the complete dissolution |
| --- | --- | --- |
| 1 | 7 | 3-6 min |
| 2 | 9 | 12-18 min |
| 3 | 11 | 40-70 min |
| 4 | 13 | 3-4 h |
| 5 | 18 | more than 24 h |

EXAMPLE 4

The samples of fluorescently labelled microspheres differing in the duration of reaction with 1-chloro-2,3-epoxypropane were prepared by the same procedure as in example 3; 0.4 ml of the sterile suspension of microspheres containing 40 mg of the dry gel was applied to rats with live weight ranging from 180 to 200 g through the superficially disinfected abdominal wall into peritoneal cavity. The rats were killed in suitable time intervals (3 rats in each time interval and per each microsphere sample), the abdominal cavity was rinsed with physiologic saline, and the sediment of irrigation as well as the surface of abdominal cavity were investigated for the presence of fluorescent microspheres. Table 2 surveys the time course of the degradation of microspheres in the abdominal cavity of rats in vivo.

EXAMPLE 5

The microspheres were prepared in the same way as in Example 2. To 5 ml of suspension containing 200 mg of gel in water, there was added 43 mg of sodium periodate ($NaIO_4$) and the suspension was agitated by shaking in darkness at 22° C. for 2 hours. The microspheres were washed on a filter with distilled water until the reaction of iodine after addition of potassium iodide dissappeared, then washed with sterile physiologic saline, and redispersed in 5 ml of the solution containing 5,000 I.U. of human chorionic genadotropin (Sigma) and adjusted with 0.1 mol $1^{-1}$ phosphate buffer to pH 7.2. The suspension was agitated by shaking at 4° C. for 4 hours and then washed with sterile physiologic saline. The washed particles were divided into three fractions and incubated a) in the phosphate buffer at pH 7.4, b) in the phosphate buffer at pH 6.2, c) in the phosphate buffer at pH 6.2 with addition of 1.5 U/ml of $\alpha$-amylase. The released chorionic gonadotropin was determined in the solution by radioimmuno assay. The rate of release of gonadotropin into medium increased in the sequence (a), (b), (c).

TABLE 2

Evaluation Of The Degradation Process Of Microspheres In Abdominal Cavity.

| Sample | Reaction time with 1-chloro-2,3-epoxypropane | Average diameter of particles | Description of Finding |
|---|---|---|---|
| 1 | 7 | 240 μm | The integral particles dissappear from the peritoneal cavity before 6 hours. The soluble fluorescent material can be detected in urine and urinary bladder. |
| 2 | 9 | 210 μm | Sporadic integral particles are present in the irrigation of perit cavity after 24 h together with the soluble fluorescent material from urine and urinary tract. |
| 3 | 11 | 162 μm | After 72 h since application, most particles in the irrigation are without visible changes in size and shape; some particles have traces of degradation. After 6 days since application, particles are found in a progressive stage of degradation; numerous macrophages containing phagocytosed fluorescent material occur in cytoplasm. The soluble fluorescent material is excreted with urine. On the 21st day since application, complete dissappearance of the particles from perit. cavity; dissappearance of the fluorescent material from cytoplasm of leucocytes present in perit. irrigation |
| 4 | 18 | 180 μm | On the 21st day after application: most of the particles in the sediment of irrigation without signs of degradation. Some particles have an injured surface - dissolving circumference. On the 40th day after application: the particles present in irrigation show a progressive state of degradation. |

EXAMPLE 6

Into 10 ml of black Chinese ink, there was added 4 g of gelatine and which was allowed to swell overnight. The gelatine was then dissolved by heating on a water bath and the solution was added into 40 ml of 1,2-dichloroethane containing 80 mg of poly(γ-methyl-L-glutamate), which was saponified to 8 mol. %, and heated to 45° C. The stirrer speed was set as in Example 1 so that the average particle size was 120 to 150 um. Then, 5 ml of 1,6hexanediisocyanate was slowly added into the reaction vessel; the stirring was continued for an additional 4 hours, and at ambient temperature for another 18 hours. Further processing of particles was carried out as in Example 1. The particles were washed with physiological saline until the reaction on amines dissappeared.

EXAMPLE 7

The spherical particles were prepared by the procedure described in example 1 with the distinction that 1.5 g of iron trioxide ($Fe_2O_3$) with particle size below 1 um was added into the solution of starch and thoroughly dispersed in this solution.

EXAMPLE 8

The microspheres prepared by the procedure according to Example 2 were dispersed in the isotonic solution of sodium chloride and sterilized in an autoclave at 120° C. for 30 min. The sterile suspension in the amount of 1 ml containing 12 mg of microspheres with diameter 150-250 um was applied into the retrouterinal space of the women to be tested. The microspheres transported through the fallopian tube were identified in the samplings of uterinal and cervical secreta under a binocular magnifier according to a yellow-green fluorescence at illumination with mercury lamp (HBO lamp). The examined set comprised 86 female patients with idiopathic sterility, where the investigations of tubal transport was indicated for the purpose of therapy. The set consists of patients who were previously examined concerning the function of the fallopian tube either by chromopertunation in laparoscopy or by hysterosalpingography and the fallopian tube were diagnosed as permeable for liquid in all cases. With the application of microspheres, the undamaged transport function of the fallopian tube was proven in the given set in 38 cases, i.e. 44%. In this group, the microspheres were unambiguously proven to be present in the samplings of cervical and uterinal secreta during 38 to 56 hours after application, irrespective of the period of ovulation cycle.

We claim:

1. A diagnostic preparation for use in investigation of the transport function of a female fallopian tube, comprising a suspension of particles in a vehicle, wherein said particles (1) have a spherical shape with a diameter from about 10 to about 600 um, (2) are formed from a soft hydrophilic gel based on a crosslinked, nontoxic, biodegradable polymer selected from (a) polysaccharides which contain glucose bound predominantly throughb 1,4 glycoside bonds, (b) polyamino acids derived from glutamic acid or aspartic acid, and (c) polypeptides which are soluble derivatives of collagen or elastin, and (3) retain their shape and size in the environment of a peritoneal cavity and a uterotubal tract for at least 80 hours and subsequently degrade to nontoxic products within 5 to 60 days in such an environment, and said vehicle is a physiologically acceptable vehicle suitable for parenteral injection.

2. The preparation of claim 1 wherein the biodegradable polymer is a polysaccharide.

3. The preparation of claim 1 wherein the biodegradable polymer is a poly(amino acid) or a polypeptide.

4. The preparation of claim 1 wherein the particles have a chromophoric or fluorophoric compound covalently bound to the polymeric compound of the particles.

5. The preparation of claim 1 wherein an additional substance which influences a biological property is bonded to the particles, said substance being selected from the group consisting of poly(amino acids), polypeptides, and hormones.

6. A method for the preparation of a diagnostic preparation for use in investigation of the transport function of a female fallopian tube, comprising dispersing, in a nonpolar, water-immiscible solvent, an aqueous suspension of a nontoxic, biodegradable polymer selected from (a) polysaccharides which contain glucose bound predominantly throughb 1,4 glycoside bonds, (b) polyamino acids derived from glutamic acid or aspartic acid, and (c) polypeptids which are soluble derivatives of collagen or elastin, said nonpolar, water-immiscible solvent containing from 0.1 to 10 wt. % of a polymeric suspension stabilizer, said dispersing being with mixing sufficient to form polymeric spherical particles having diameters from 10 to 600 um, transforming the particles into a gel state by contacting the same with a bifunctional crosslinking agent, washing the same with an alkaline aqueous solution, and dispersing the particles in a vehicle which is suitable for parenteral administration.

7. The method of claim 6 wherein the suspension stabilizer contains 80–100 mol. % of gamma-alkyl-L-glutamate units and 0–20 mol. % of L-glutamic acid.

8. The method of claim 6 further comprising the step of chemically activating the particles for binding with biologically active peptides.

9. The method of claim 6 wherein the aqueous suspension also contains an aminoacyl derivative of a fluorochrome, a dispersed pigment, or magnetic particles, in an amount from 0 to about 10 wt. %.

* * * * *